United States Patent
Giordano et al.

[11] Patent Number: 5,223,612
[45] Date of Patent: Jun. 29, 1993

[54] PROCESS FOR THE PREPARATION OF BENZOTHIAZEPINES BY CYCLIZATION WITH PHOSPHONIC ACIDS

[75] Inventors: Claudio Giordano, Monza; Maurizio Paiocchi, Milan, both of Italy

[73] Assignee: Zambon Group S.p.A., Vicenza, Italy

[21] Appl. No.: 882,512

[22] Filed: May 13, 1992

[30] Foreign Application Priority Data

May 23, 1991 [IT] Italy .................. 001426 A/91

[51] Int. Cl.$^5$ ............................... C07D 281/02
[52] U.S. Cl. .................................... 540/491
[58] Field of Search ............................. 540/491

[56] References Cited

U.S. PATENT DOCUMENTS

5,128,469  7/1992  Nishimoto et al. ............. 540/491

FOREIGN PATENT DOCUMENTS

0378455  7/1990  European Pat. Off. ......... 540/491
0447135  3/1991  European Pat. Off. ......... 540/491
0415384  9/1991  European Pat. Off. ......... 540/491

OTHER PUBLICATIONS

H. Wissmann et al "New Peptide Synthesis", *Angewandte Chemie International Edition In English*, vol. 19, No. 2, (1980) pp. 133–134.

The Merck Index *An Encyclopedia of Chemicals, Drugs, and Biologicals*, 11th Ed. (1989), Abstract No. 3188.

Blackburn, et al "The Dealkylation of Phosphate and Phosphonate Esters By Iodotrimethylsilane: A Mild and Selective Procedure". *J.C.S. Perkin I*, (1980) pp. 1150–1153.

Chemical Abstracts, vol. 99, (1983), p. 577, Abstract No. 99:53972u.

Chemical Abstracts, vol. 106, (1987) p. 437, Abstract No. 106:4672a.

*Primary Examiner*—Robert T. Bond
*Attorney, Agent, or Firm*—Stevens, Davis, Miller & Mosher

[57] ABSTRACT

Process for the preparation of (2S,3S)-2,3-dihydro-3-hydroxy-2-(4-methoxyphenyl)-1,5-benzothiazepin-4(5H)-one of formula

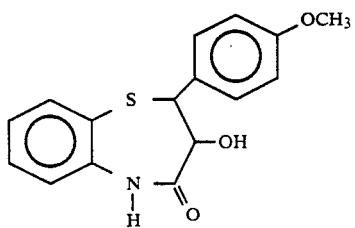

by direct cyclization of the compound of the formula

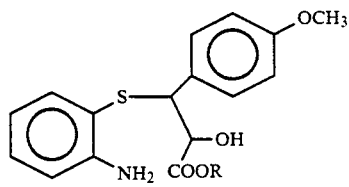

with a catalytic amount of phosphonic acid.

5 Claims, No Drawings

PROCESS FOR THE PREPARATION OF BENZOTHIAZEPINES BY CYCLIZATION WITH PHOSPHONIC ACIDS

A process for the preparation of (2S,3S)-2,3-dihydro-3-hydroxy-2-(4-methoxyphenyl)-1,5-benzothiazepin-4(5H)-one (compound I) by cyclization of an intermediate of formula

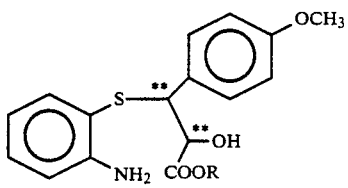

wherein R represents a $C_1$–$C_3$ alkyl and the asterisks identify the asymmetric carbon atoms; is described.

Compound I is an intermediated useful in the synthesis of Diltiazem.

The present invention relates to a process for the synthesis of benzothiazepines and more particularly it relates to a process for the preparation of (2S,3S)-2,3-dihydro-3-hydroxy-2-(4-methoxyphenyl)-1,5-benzothiazepin-4(5H)-one of formula

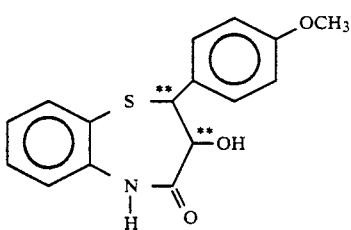

wherein the asterisks identify the asymmetric carbon atoms; a useful intermediate for the synthesis of Diltiazem. Diltiazem is the International Nonproprietary Name (INN) of the compound (2S,3S)-5-[2-dimethylamino-ethyl]-3-acetoxy-2,3-dihydro-2-(4-methoxyphenyl)-1,5-benzothiazepin-4(5H)-one hydrochloride (Merck Index, XI Ed., No. 3188, page 505) which is a known drug with calcium-antagonist activity.

Several methods for the preparation of Diltiazem are known in the literature.

Most of them foresee the preparation of an intermediate of formula

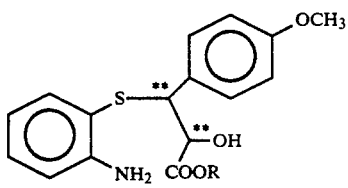

wherein R represents a $C_1$–$C_3$ alkyl and the asterisks identify the asymmetric carbon atoms; which is then cyclized for obtaining the compound of formula I. This latter affords Diltiazem by alkylation and acetylation (British patent application No. 2,139,620 in the name of Shionogi Saiyaku Kabushiki Kaisha).

Generally the ester of formula II is hydrolyzed to the corresponding free acid before the cyclization to compound I [Japanese patent application No. 61/145159 in the name of Nippon Chemiphar K.K. (C.A., 106:4672a)].

However it would be convenient to have available a method that allows the direct cyclization of the ester of formula II.

In fact, in this way, the number of the steps necessary for the preparation of Diltiazem would be lower and the whole process would be economically more convenient.

A method that makes use of a sulfonic acid or phosphoric acid, such as for example methanesulphonic acid, for obtaining the direct cyclization of the ester of formula II without separating the corresponding acid (European patent application No. 378455 in the name of Synthelabo) has been described.

However, phosphoric acid does not appear to be suitable because it is not in homogeneous phase during the reaction, while the sulfonic acid affords a cyclization product which is not sufficiently pure, it is coloured, and must be purified for obtaining a compound useful for the preparation of Diltiazem having characteristics as requested by the pharmacopoeiae, thus the yields are lowered.

We have found and it is object of the present invention a process for the preparation of (2S,3S)-2,3-dihydro-3-hydroxy-2-(4-methoxyphenyl)-1,5-benzothiazepin-4(5H)-one of formula

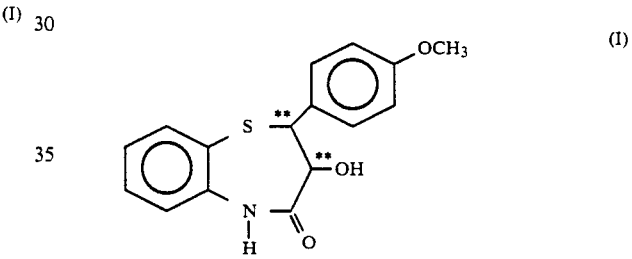

wherein the asterisks identify the asymmetric carbon atoms; which comprises the direct cyclization of the compound of formula

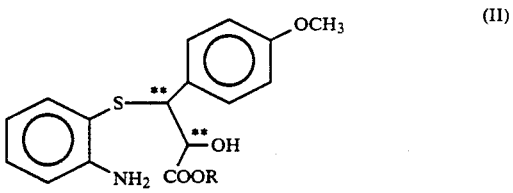

wherein R represents a $C_1$–$C_3$ alkyl and the asterisks identify the asymmetric carbon atoms;

with a catalytic amount of a phosphonic acid of formula $$R_1\text{-}PO_3H_2 \qquad (III)$$

wherein $R_1$ represents a $C_1$–$C_5$ alkyl or $C_2$–$C_5$ alkenyl, in an inert solvent.

The process object of the present invention is useful for preparing compounds with calcium-antagonist activity.

The compounds of formula II are prepared according to techniques known in the literature.

For example in the European patent No. 59335 in the name of Tanabe Seiyaku Co. Ltd. the preparation of compound of formula II by reaction with an ester of 3-(4-methoxyphenyl)-glycidic acid and 2-nitrophenol and subsequent reduction of the nitro-group is described.

The preferred compound of formula II is that in which R represents methyl.

Examples of phosphonic acids of formula III are methyl-phosphonic acid, vinyl-phosphonic acid, cis-1-propenyl-phosphonic acid, isobutyl-phosphonic acid, n-pentyl-phosphonic acid.

Phosphonic acids of formula III are known or obtainable according to known methods [for example C.A. 99:53972u (Japanese patent application No. 58/52299 in the name of Meiji Seika Kaisha Ltd.); J. Chem.

Soc. Perkin I, No. 5,1150, (1980)]. Among these the preferred one is cis-1-propenyl-phosphonic acid. Generally, it is preferable to use the acid in a molar ratio of 0.01–0.5 with respect to compound II and preferably in a molar ratio of 0.05–0.1.

The cyclization reaction is carried out in an inert solvent such as for example an aromatic hydrocarbon, in particular xylene, toluene, chlorobenzene, or a chlorinated hydrocarbon, in particular 1,1,2,2-tetrachloroethane and preferably at reflux temperature.

At the end of the reaction the compound of formula I can be isolated as pure product by a simple and easy work-up.

The process object of the present invention gives the desired product with good yields, slightly higher than those of the process described in EP 378455, by direct cyclization of the ester of formula II.

It is worth noting that the experimental conditions used in the cyclization reaction allow to obtain the optically active compound I with high enantiomeric purity directly from the optically active compound II thus avoiding so further resolution steps.

Moreover, the product thus obtained is very pure and does not need to be purified for obtaining Diltiazem having characteristics as requested by the pharmacopoeiae.

Thus, the limited number of steps required, the possibility to isolate the product by simple and easy operations, the good yields and the high purity so obtained make the process object of the present invention particularly convenient from an industrial point of view.

With the aim to better illustrate the present invention without limiting it in any way the following examples are now given.

EXAMPLE 1

Preparation of
(2S,3S)-2,3-dihydro-3-hydroxy-2-(4-methoxyphenyl)-
1,5-benzothiazepin-4(5H)-one A mixture of (2S,3S)-2-hydroxy-3-(2-aminophenyl-thio)-3-(4-methoxyphenyl)-propionic acid methyl ester (5 g; 15 mmol) ($[\alpha]^{20}_D = +99°$; c=1% in CHCl$_3$) and cis-1-propenyl-phosphonic acid (0.183 g; 1.5 mmol) in xylene (35 ml) was heated under reflux and under stirring for 5.5 hours.

The mixture was then distilled by collecting a mixture of xylene and methanol (about 3%).

The reaction mixture was then cooled to 15° C.

A precipitate was obtained which was filtered under vacuum, washed with xylene (2×5 ml) and dried in oven (65° C.).

(2S,3S)-2,3-dihydro-3-hydroxy-2-(4-methoxyphenyl)-1,5-benzothiazepin-4(5H)-one (4.2 g; HPLC titre 98%; 89.6% yield) was obtained.

EXAMPLE 2

Preparation of
(2S,3S)-2,3-dihydro-3-hydroxy-2-(4-methoxyphenyl)-
1,5-benzothiazepin-4(5H)-one A mixture of (2S,3S)-2-hydroxy-3-(2-amino-phenyl-thio)-3-(4-methoxyphenyl)-propionic acid methyl ester (5 g; 15 mmol) ($[\alpha]^{20}_D = +99°$; c=1% in CHCl$_3$) and cis-1-propenyl-phosphonic acid (0.091 g; 0.75 mmol) in xylene (35 ml) was heated under reflux and under stirring for 5.5 hours.

The mixture was distilled by collecting a mixture of xylene and methanol.

The reaction mixture was then cooled to 15° C.

A precipitate was obtained which was filtered under vacuum, washed with xylene (2×5 ml) and dried in oven (65° C.).

(2S,3S)-2,3-dihydro-3-hydroxy-2-(4-methoxyphenyl)-1,5-benzothiazepin-4(5H)-one (4 g; HPLC titre 99.5%; 88.45% yield) was obtained.

EXAMPLE 3

Preparation of
(2S,3S)-2,3-dihydro-3-hydroxy-2-(4-methoxyphenyl)-
1,5-benzothiazepin-4(5H)-one A mixture of (2S,3S)-2-hydroxy-3-(2-amino-phenyl-thio)-3-(4-methoxyphenyl)-propionic acid methyl ester (200 g; 600 mmol) ($[\alpha]^{20}_D = +99°$; c=1% in CHCl$_3$) and cis-1-propenyl-phosphonic acid (2.93 g; 24 mmol) in xylene (1340 ml) was reflux heated, under stirring.

The mixture was distilled, by collecting the mixture of xylene and methanol (about 50 ml) in 11 hours.

The reaction mixture was then cooled to 15° C.

A precipitate obtained which was filtered, washed with xylene (100 ml+50 ml) and dried in oven (65° C.) under vacuum.

(2S,3S)-2,3-dihydro-3-hydroxy-2-(4-methoxyphenyl)-1,5-benzothiazepin-4(5H)-one (163 g; HPLC titre 100%; 90.3% yield) was obtained.

On the basis of HPLC analysis the mother liquors contained further (2S,3S)-2,3-dihydro-3-hydroxy-2-(4-methoxyphenyl)-1,5-benzothiazepin-4(5H)-one (2.35 g).

EXAMPLE 4

Preparation of
(2S,3S)-2,3-dihydro-3-hydroxy-2-(4-methoxyphenyl)-
1,5-benzothiazepin-4(5H)-one A mixture of (2S,3S)-2-hydroxy-3-(2-aminophenyl-thio)-3-(4-methoxyphenyl)-propionic acid methyl ester (50 g; 150 mmol) ($[\alpha]^{20}_D = +99°$; c=1% in CHCl$_3$) and isobutyl-phosphonic acid (0.415 g; 3 mmol) in xylene (167 ml) was reflux heated under stirring for 12 hours.

The mixture was then distilled by collecting a mixture of xylene and methanol.

The reaction mixture was then cooled to 15° C.

A precipitate was obtained which was filtered under vacuum, washed with xylene (2×20 ml) and dried in oven (65° C.).

41.77 g of a crude was obtained, which on the basis of HPLC analysis contained (2S,3S)-2,3-dihydro-3-hydroxy-2-(4-methoxyphenyl)-1,5-benzothiazepin-4(5H)-one (30.7 g).

The starting product (11 g) was also collected.

We claim:

1. A process for the preparation of (2S,3S)-2,3-dihydro-3-hydroxy-2-(4-methoxyphenyl)-1,5-benzothiazepin-4(5H)-one of formula

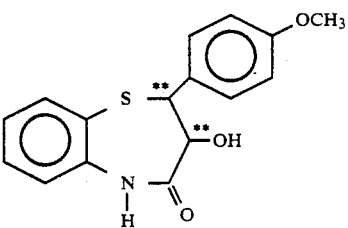

wherein the asterisks identify the asymmetric carbon atoms; which comprises the direct cyclization of the compound of formula

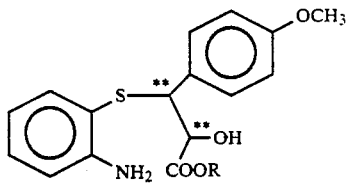

wherein R represents a $C_1$–$C_3$ alkyl and the asterisks identify the asymmetric carbon atoms;
with a catalytic amount of a phosphonic acid of formula $$R_1\text{-}PO_3H_2 \qquad (III)$$

wherein $R_1$ represents a $C_1$–$C_5$ alkyl or $C_2$–$C_5$ alkenyl in an inert solvent.

2. A process according to claim 1 wherein the phosphonic acid of formula III is selected among methyl-phosphonic acid, vinyl-phosphonic acid, cis-1-propenyl-phosphonic acid, isobutyl-phosphonic acid, n-pentyl-phosphonic acid.

3. A process according to claim 1 wherein the phosphonic acid of formula III is cis-1-propenyl-phosphonic acid.

4. A process according to claim 1 wherein the reaction is carried out at the reflux temperature of the inert solvent.

5. A process according to claim 2 wherein the phosphonic acid of formula III is cis-1-propenyl-phosphonic acid.

* * * * *